United States Patent
Horn et al.

(10) Patent No.: US 9,427,151 B2
(45) Date of Patent: *Aug. 30, 2016

(54) ULTRA WIDE-FIELD OPTICAL COHERENCE TOMOGRAPHY

(71) Applicant: Carl Zeiss Meditec, Inc., Dublin, CA (US)

(72) Inventors: Jochen M. M. Horn, San Francisco, CA (US); Andre Malz, Dublin, CA (US); Christopher J. R. V. Baker, Moraga, CA (US); Oliver Wirth, Stuttgart (DE)

(73) Assignee: CARL ZEISS MEDITEC, INC., Dublin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/598,017

(22) Filed: Jan. 15, 2015

(65) Prior Publication Data

US 2015/0124219 A1    May 7, 2015

Related U.S. Application Data

(63) Continuation of application No. 13/458,933, filed on Apr. 27, 2012, now Pat. No. 8,960,903.

(60) Provisional application No. 61/479,799, filed on Apr. 27, 2011.

(51) Int. Cl.
*A61B 3/14* (2006.01)
*A61B 3/00* (2006.01)
(Continued)

(52) U.S. Cl.
CPC .............. *A61B 3/102* (2013.01); *A61B 3/0075* (2013.01); *A61B 3/0083* (2013.01); *A61B 3/1025* (2013.01); *A61B 3/113* (2013.01); *A61B 3/1225* (2013.01); *A61B 3/152* (2013.01)

(58) Field of Classification Search
CPC ........ A61B 3/103; A61B 3/14; A61B 3/152; A61B 3/113; A61B 3/1208; A61B 3/135; A61B 3/0285; A61B 3/1225; A61B 3/024; A61B 3/1015

USPC ........ 351/200, 205–206, 208–210, 213–214, 351/217, 221–222, 246
See application file for complete search history.

(56) References Cited

U.S. PATENT DOCUMENTS

| 4,933,756 | A | 6/1990 | Sekine |
| 5,815,242 | A | 9/1998 | Anderson et al. |

(Continued)

FOREIGN PATENT DOCUMENTS

| JP | 54-33392 A | 3/1979 |
| JP | 62-31941 B2 | 7/1987 |

(Continued)

OTHER PUBLICATIONS

Office Action received for European Patent Application No. 12719642.6, mailed on Jul. 13, 2015, 5 pages.

(Continued)

*Primary Examiner* — Dawayne A Pinkney
(74) *Attorney, Agent, or Firm* — Morrison & Foerster LLP

(57) ABSTRACT

Systems and methods for expanding the field-of-view of ophthalmic scanning devices are presented. An ophthalmic scanning device is designed such that the pivot point of the scanning optics is maintained at a fixed location in the pupil while the scanning optics are rotated about the eye to obtain imaging data over an increased field-of-view than can be achieved by the scanning optics alone. The rotation can be achieved using a singular rotational motion of the scanning optics about a rotational axes coincident with the scanning pivot point or can be achieved using a combination of rotational motion with a second motion either rotational or translational to maintain the scanning pivot point at the fixed location. Embodiments related to optical coherence tomography and scanning laser ophthalmoscopy are described.

22 Claims, 2 Drawing Sheets

(51) Int. Cl.
   *A61B 3/10* (2006.01)
   *A61B 3/113* (2006.01)
   *A61B 3/15* (2006.01)
   *A61B 3/12* (2006.01)

(56) References Cited

U.S. PATENT DOCUMENTS

| | | |
|---|---|---|
| 5,847,807 A | 12/1998 | Steinmetz |
| 5,943,116 A | 8/1999 | Zeimer |
| 7,401,921 B2 | 7/2008 | Baker et al. |
| 7,884,945 B2 | 2/2011 | Srinivasan et al. |
| 2001/0022850 A1 | 9/2001 | Yang et al. |
| 2003/0095081 A1 | 5/2003 | Furness, III et al. |
| 2007/0291277 A1 | 12/2007 | Everett et al. |
| 2008/0088938 A1 | 4/2008 | Lai |
| 2008/0100612 A1 | 5/2008 | Dastmalchi et al. |
| 2009/0093798 A1 | 4/2009 | Charles |
| 2010/0149490 A1 | 6/2010 | Olivier et al. |
| 2010/0225883 A1 | 9/2010 | Ho et al. |
| 2010/0328606 A1 | 12/2010 | Peyman |
| 2011/0234977 A1 | 9/2011 | Verdooner |
| 2012/0083772 A1 | 4/2012 | Rubinfeld et al. |
| 2012/0274897 A1 | 11/2012 | Narasimha-Iyer et al. |

FOREIGN PATENT DOCUMENTS

| | | |
|---|---|---|
| JP | 2002-34925 A | 2/2002 |
| WO | 95/13012 A2 | 5/1995 |

OTHER PUBLICATIONS

Third party Observation Under Article115 EPC received for European Patent Application No. 12719642.6, mailed on Jun. 3, 2015, 3 pages.

International Search Report and Written Opinion received for PCT Patent Application No. PCT/EP2012/057748, mailed on Aug. 22, 2012, 9 pages.

Non-Final Office Action received for U.S. Appl. No. 13/458,933, mailed on Dec. 6, 2013, 13 pages.

Final Office Action received for U.S. Appl. No. 13/458,933, mailed on Apr. 15, 2014, 14 pages.

Notice of Allowance received for U.S. Appl. No. 13/458,933, mailed on Oct. 16, 2014, 10 pages.

Notice of Allowance received for U.S. Appl. No. 13/458,933, mailed on Dec. 18, 2014, 5 pages.

An et al., "High-Resolution Wide-Field Imaging of Retinal and Choroidal Blood Perfusion with Optical Microangiography", Journal of Biomedical Optics, vol. 15, No. 2, Mar./Apr. 2010, pp. 026011-1-026011-9.

Hackel et al., "Creating Retinal Fundus Maps", The Journal of Ophthalmic Photography, vol. 27, No. 1, Spring 2005, pp. 10-18.

Kaines et al., "Ultrawide Angle Angiography for the Detection and Management of Diabetic Retinopathy", International Ophthalmology Clinics, vol. 49, No. 2, 2009, pp. 53-59.

Leitgeb et al., "Ultrahigh Resolution Fourier Domain Optical Coherence Tomography", Optics Express, vol. 12, No. 10, May 17, 2004, pp. 2156-2165.

Li et al., "Automatic Montage of SD-OCT Data Sets", Optics Express, vol. 19, No. 27, Dec. 19, 2011, pp. 26239-26248.

ULTRA WIDE-FIELD OPTICAL COHERENCE TOMOGRAPHY

PRIORITY

This application is a continuation of U.S. patent application Ser. No. 13/458,933, filed Apr. 27, 2012 and also claims priority to U.S. Provisional Application Ser. No. 61/479,799 filed Apr. 27, 2011, the contents of which are both hereby incorporated by reference.

TECHNICAL FIELD

One or more embodiments of the present invention are directed towards improvements in scanning ophthalmic imaging systems. In particular, embodiments of the invention include systems and methods for increasing the field-of-view and enabling automated scanning of wide areas of the patient's eye. Embodiments related to optical coherence tomography (OCT) and scanning laser ophthalmoscopy (SLO) are considered.

BACKGROUND

Optical coherence tomography (OCT) and scanning laser ophthalmoscopy (SLO) are cross-sectional, non-invasive imaging modalities, that have been developed for diverse areas of medical imaging. In ophthalmology, both have been used for imaging the retina, choroid and anterior segment of the eye and providing valuable clinical information on the eye's condition. Because the time a patient can maintain the eye in a fixed position is limited, tradeoffs between image resolution and the area covered in a scan have been required. In the past, ophthalmic imaging instruments using scanning modalities have typically enlarged the field-of-view by expanding the size of the optics and opto-mechanical elements, a strategy that incurs considerable cost. Attempts have also been made to expand the field-of-view by allowing the user to stitch together multiple fundus images in post processing (see for example i2k Retina™, DualAlign™ LLC, Clifton Park, N.Y.).

SUMMARY

It is an object of the present invention to achieve a very large field-of-view in ophthalmic scanning devices (OSDs) thereby achieving high quality, wide-field imaging without the disadvantages of costly optics and mechanics and with high flexibility. This is achieved by moving the instrument relative to the eye while collecting a series of imaging data in a fashion that ensures that the optical scanning pivot point and the rotary axis or axes of the device remain in approximate coincidence with the patient's pupil center. This co-location of the two pivot points (the optical scanning pivot point and the device's rotary pivot point) with the patient's pupil center, or other point within the pupil, allows placement of OSD scans over wide areas of the retina, even up to the periphery, without apodization and refocusing. The device's rotary pivot point can be located along an actual axis of rotation of the instrument or a virtual pivot point achieved via a controlled combination of translational and rotational adjustments of the instrument. Due to the active control of the co-localization using an independent pupil imaging device (such as an iris camera), the imaging procedure can be automated to allow for stitching of OSD scans to generate line, area or cube scans of largely unlimited length or area of the retina, and placement of scans at any location on the human retina that is optically accessible.

DETAILED DESCRIPTION

The invention described herein allows for a wide field-of view in optical scanning imaging of the eye without employing specialized and costly optics and opto-mechanics or user-changeable optics. The invention can be used for any type of ophthalmic scanning device (OSD) including but not limited to optical coherence tomography (OCT), scanning laser ophthalmoscopy (SLO) imaging or combinations thereof. OSDs are capable of generating 1D, 2D, or 3D imaging data that are used by doctors to view and diagnose various pathologies in the eye.

Fourier-domain OCT (FD-OCT), sometimes referred to as frequency-domain OCT, has recently attracted attention because of its high sensitivity and imaging speed compared to time-domain OCT (TD-OCT), which uses an optical delay line for mechanical depth scanning with a relatively slow imaging speed. The spectral information discrimination in FD-OCT is accomplished either by using a dispersive spectrometer in the detection arm (spectral domain OCT) or rapidly scanning a swept laser source (swept-source OCT). The invention described herein could be applied to all types of OCT imaging as well as laser scanning imaging using point scanning or line scanning and includes combinations of OCT and SLO.

Figure 1:
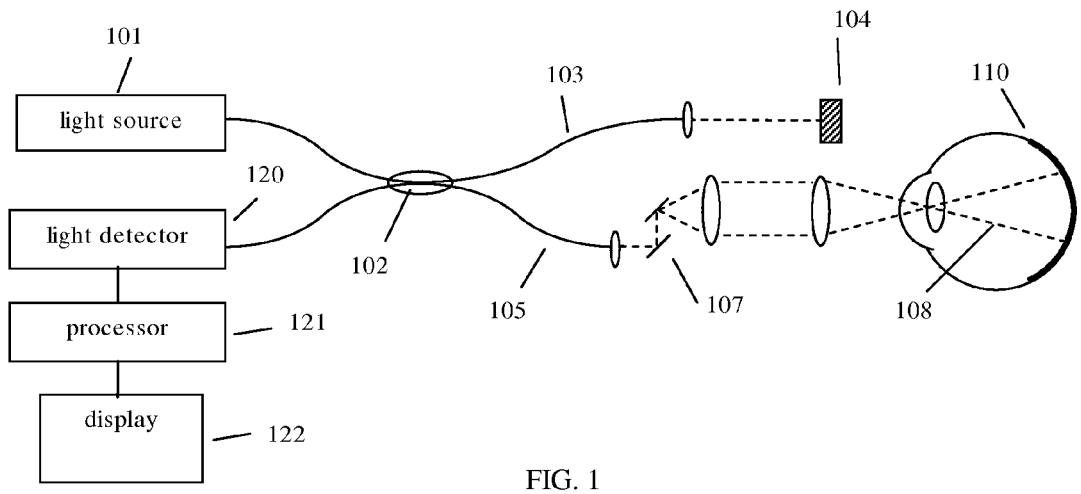
FIG. 1 illustrates a generalized optical coherence tomography scanning device that can be used in some embodiments of the present invention.

A generalized optical coherence tomography device that could be used in some embodiments of the present invention is illustrated in FIG. 1. The light source 101 can be either a broadband light source with short temporal coherence length or a swept laser source. Light from source 101 is routed, typically by optical fiber 105, to illuminate the sample 110, a typical sample being tissues in the human eye. The light is scanned, typically with a scanner 107 between the output of the fiber and the sample, so that the beam of light (dashed line 108) is scanned laterally (in x and y) over the area or volume to be imaged. Light scattered from the sample is collected, typically into the same fiber 105 used to route the light for sample illumination. Reference light derived from the same source 101 travels a separate path, in this case involving fiber 103 and retro-reflector 104. Those skilled in the art recognize that a transmissive reference path can also be used. Collected sample light is combined with reference light, typically in a fiber coupler 102, to form light interference in a detector 120. The output from the detector is supplied to a processor 121. The results can be stored in the processor or displayed on display 122. The Fourier transform of the interference light reveals the profile of scattering intensities at different path lengths, and therefore scattering as a function of depth (z-direction) in the sample (see for example Leitgeb et al, "Ultrahigh resolution Fourier domain optical coherence tomography," *Optics Express* 12(10):2156 2004). The profile of scattering as a function of depth is called an axial scan (A-scan). A set of A-scans measured at neighboring locations in the sample produces a cross-sectional image (tomogram or B-scan) of the sample. A collection of B-scans makes up a data cube or cube scan.

A SD-OCT system is described in detail in US Patent Publication No. 2007/0291277 and is hereby incorporated by reference. In this system an iris viewer provides an image of the pupil of the eye that is used primarily to align the patient's eye with the optical axis of the device. This is one way to achieve pupil position detection that is an aspect of several embodiments of the present invention.

The present invention describes an OSD, such that the device's scanning pivot point falls in the center of the patient's pupil or its vicinity. Such a device could be telecentric. The device's scanning pivot point can be pre-aligned with each actual or virtual rotary axis (typically horizontal and/or vertical) of the device. Each actual or virtual rotary axis can then be moved to provide a pivot point in the patient's pupil. In this way the device can be moved, either manually or automatically, in either or multiple directions (for example swivel for horizontal direction or tilt for vertical direction), without the patient being required to move while collecting imaging data covering a wide field-of-view. A type of virtual rotary axis could be realized by attaching the device to a curved rail where the pupil location is at the center of the radius of curvature. A virtual rotary axis can also be realized by an angular movement about an axis that is not collinear with an axis lying in the pupil but, when coupled with translation or an additional axis of rotation, can provide the effect of collinearity.

The use of a virtual rotary axis has several advantages. First, it is difficult to provide pivot points that are lying within the eye. A horizontal axis through a pivot point in the pupil for instance would have to be beside the patient's temples and a vertical axis through a pivot in the pupil would have to be under the chin—both positions that invade the comfort zone of the patient. Secondly, this technique allows the pivot point to be moved such that it can be centered in the pupil or offset anywhere within the pupil; this can be useful for avoiding opacities typically caused by cataract. A disadvantage of this technique is that angular and translational motion must be coupled. If, however, motor drives are used to provide the motions, an algorithm can be developed to couple the motions of the motors such that the movement will appear to be that of a swivel/tilt located at the pupil. The ability to cover extremely large areas on the retina with OCT scans is currently available only with very expensive and specialized OSDs in the ophthalmic diagnostic equipment market.

Figure 2:
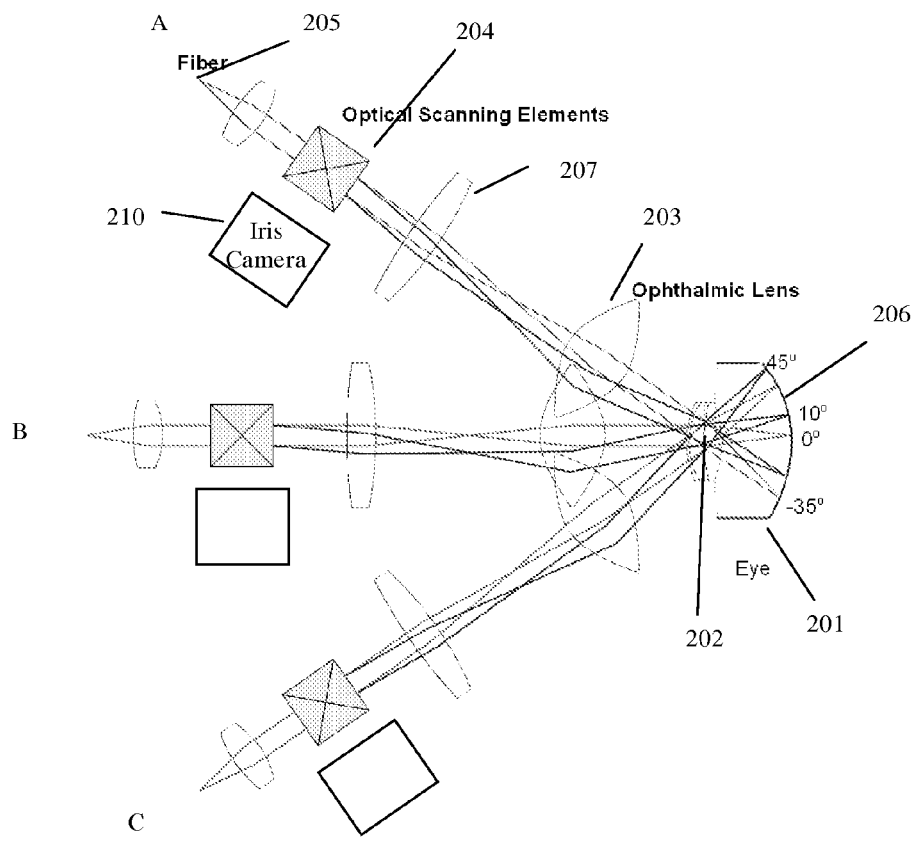
FIG. 2 illustrates the achievable field-of-view in ophthalmic imaging using aspects of the present invention.

In one embodiment of the present invention, the OSD includes a sample scanning arm configured as shown in FIG. 2. The scanning arm, also referred to as the optics head, includes at a minimum, the optical and opto-mechanical components responsible for directing and scanning the light onto the sample. These components can be housed in the same enclosure as the other components of the OSD (source, processor, display, driver, etc.) or may be housed separately and connected to the other components via a fiber optic 205. The optics head includes optical scanning elements, typically galvanometers, for scanning the beam in x and y directions covering a certain field of view on the retina 206 of the eye 201, typically covering a field of view on the order of 40 degrees. Additional lenses 203 and 207 are used to control the focal properties of the light. In OCT imaging of the retina, the light is typically focused within the retina.

In this embodiment, the optics head is mounted on an instrument base and includes a patient support or headrest (not shown). The base could be a slit lamp base. The headrest can be adjustable and is capable of moving the patient along three orthogonal axes. This motion could be motorized as described in U.S. Pat. No. 7,401,921 hereby incorporated by reference. Optionally the instrument could be adjusted to position itself relative to the patient in multiple axes (i.e. using a three axis motion stage). The instrument base allows positioning of the optics head independent from the patient's positioning so that the eye 201 remains fixed relative to the instrument's optics head. The instrument base in this embodiment has its base rotary pivot point located at the center of the patient's pupil 202 such that as the instrument is rotated about the pupil between locations A, B and C, the beam continues to pass through a fixed location in the pupil, in this case the center of the pupil, and achieves a wide range of locations (covering greater than 80 degrees) on the retina 206 of the eye 201. The optical scanning elements can be scanned over their field-of-view at the plurality of pupil entry angles and the resulting reflected light can be detected and combined into a single image for a plurality of pupil entry angles. The single image could achieve greater than 140 degree total field-of-view.

The figure illustrates only one axis of rotation in this case, motion along the horizontal direction or swivel. The system is rotationally symmetric so that the same is true for the vertical (tip/tilt) direction as would be visualized moving in and out of the plane of the paper. Horizontal and vertical are the typical directions of which an instrument would be rotated but in fact the invention described herein would apply equally to rotation of the instrument in any direction.

In a preferred embodiment, a pupil location detector (i.e. an iris camera 210) is added to the instrument to verify the location of the beams relative to the pupil. An iris camera as described in US Patent Publication No. 2007/0291277 involves positioning an LED having a wavelength of 700 nm near the ophthalmic lens 203. The back reflected light is directed to a CMOS camera using various optics, typically lenses and beam splitters. Other configurations can be envisioned by those skilled in the art. The images provided by the iris camera could be provided to the user to verify the alignment of the beam relative to the pupil throughout the instrument's scanning and rotation or preferably, could be analyzed by the processor to ensure that the beam location and scanning pivot point is being maintained as the optics head is rotated. Additionally internal and/or external fixation targets could be used in an effort to control the patient's fixation during the wide field imaging. It may be necessary to transition from the internal to the external fixation target as the system is rotated. It may be desirable that the external fixation target is rigidly mounted to the optics head. While the design of this embodiment involves a mechanical pivot point in line with the pupil of the eye, the rotation of the optics head could also be realized using a curved rail where the radius of curvature is designed such that the scanning pivot point is maintained in the pupil during the rotation.

In another embodiment of the invention, with the advantages of the virtual pivot point mentioned above, the OSD's optics head can be moved in swivel and tilt by separate motions that are controlled independently to realize the same rotational adjustments illustrated in FIG. 1. The optical scanning pivot point and the device's virtual pivot point are typically pre-aligned to be coincident. In addition to rotation and/or translation adjustments, the OSD includes a pupil position detection device (e.g. an iris viewer) and optionally internal and/or external fixation targets for the patient to focus on during the scanning operation. The rotational motion is carried out around a virtual rotation axis created by two or more coupled or uncoupled motions with the pivot point located in the eye's pupil as described above by combining the rotation of the optics head with a translational motion. As will be described in detail below, the translational motion can be linear or can be an arc. In the case of linear translation, the virtual rotary axis would consist of rotation and linear travel, in the case of an arc the virtual rotary axis would consist of rotation coupled with a second rotation.

Figure 3:
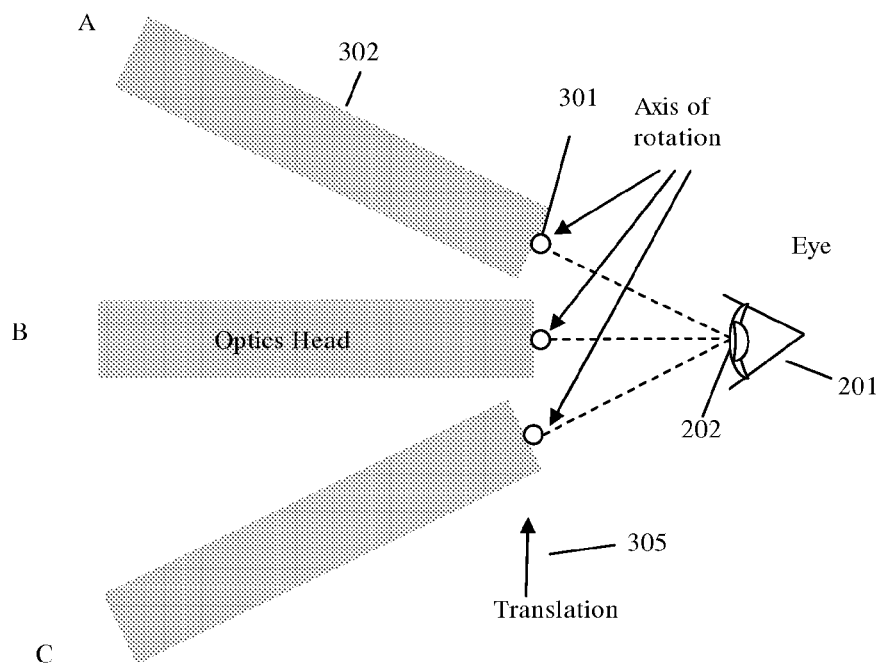
FIG. 3 illustrates an embodiment of the invention in which rotational and translational motions are combined to maintain the scanning pivot point in the pupil of the eye.

FIG. 3 illustrates the case in which the rotation of the OSD is realized using a combination of rotational and translational motions. Here the axis of rotation 301 of the optics head 302 is located at the end of the optics head closest to the patient's eye 201. The axis of rotation could be in the horizontal, vertical, or any arbitrary direction that may be desired. Pure rotation around this axis would result in the beam entry location moving with respect to the pupil 202. Here, a translational motion indicated by arrow 305 is used to maintain the desired pupil entry location and scanning pivot point as the pupil entry angle is adjusted between positions A, B, and C to collect wide field-of-view images of the eye. The figure illustrates the final position of the optics head after both the rotational and translational motion. The two translational motions can be realized using coupled mechanical mechanisms, including motors that are coupled via electronics.

Figure 4:
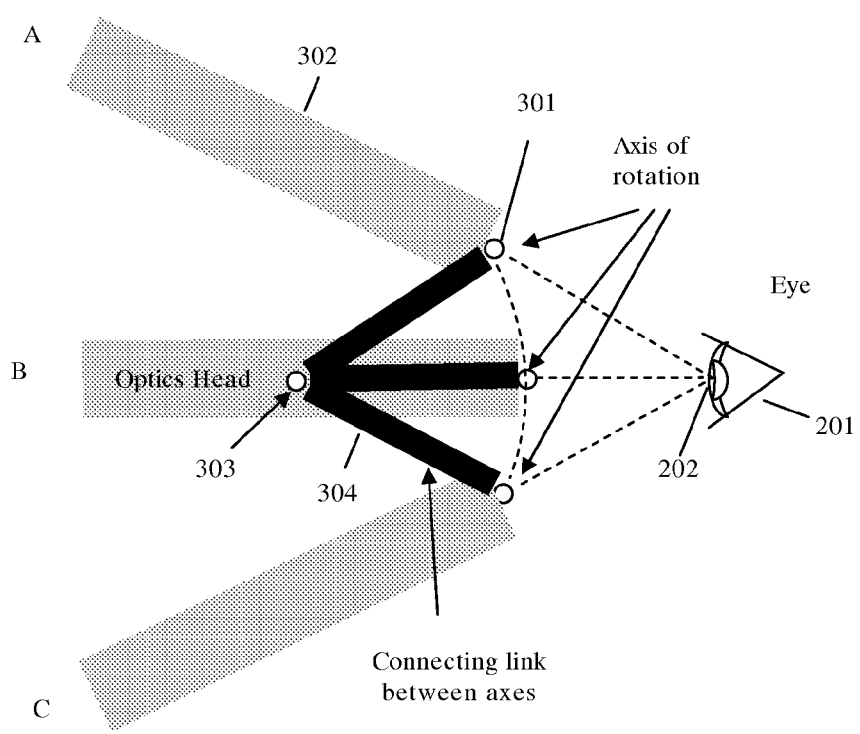
FIG. 4 illustrates an embodiment of the invention in which two rotational motions are combined to maintain the scanning pivot point in the pupil of the eye.

FIG. 4 illustrates the case in which the rotation of the OSD is realized using a combination of two rotational movements. Similar to FIG. 3, the axis of rotation 301 of the optics head 302 is located at the end of the optics head closest to the eye 201. Again the axis of rotation could be oriented in any arbitrary direction, in a preferred embodiment, horizontal and vertical, and pure rotation of the instrument head along the axis would result in movement of the device's scanning pivot point away from a set location in the pupil. In this embodiment, a second axis of rotation 303 is established for the device. This axis is fixed and does not move with the rotation of the first axis so as the optics head is rotated along the first axis, a coupled rotation occurs to result in an arc motion to maintain the scanning pivot point in the pupil. The black lines 304 illustrate the linkage between the two axes for the three different pupil entry locations A, B, and C. The figure illustrates the final position of the optics head after both rotational motions.

Typically the motions will consist of pre-determined patterns that allow large areas of the retina to be scanned while maintaining the co-localization between the instrument's scanning pivot point and the patient's pupil, which in turn can be moved to accommodate still larger areas of the retina by movement of the fixation target. The motions can be mapped out for a particular design and referenced in the processor using a "look-up table" in which the particular rotation and translation motions required are tabulated or calculated to achieve a specific pupil entry angle.

While the pre-determined pattern ensures approximate co-localization, exact co-localization is controlled and realized via the pupil imaging device as described above. Instead of exact co-localization of the scanning pivot point with the center of the eye's pupil it may be desirable to deviate slightly from this position e.g. due to cataract in the eye as described in U.S. patent application Ser. No. 13/453, 856 filed Apr. 23, 2012. One implementation of such optimized pupil positioning consists in moving the scanning pivot point in the vicinity of the point of co-localization while taking data. This fine positioning within the pupil may also follow a pre-determined pattern, the data providing an indication of the best places within the pupil to take the scan. Fine positioning can be manually or automatically controlled by feedback from the pupil imaging device to ensure that the scanning pivot point stays in a pre-defined vicinity. The optimum position can be found based on some measure of image quality, e.g. signal strength.

All pre-defined motions for positioning the OSD's optics head, whether the motions that provide tilt/swivel or the fine motions to find the optimum area of the pupil to be scanned, can be based on average as well as patient specific data (e.g. obtained during previous visits). The motion control can be fully automated or can be manual or a combination of automated and manual control (i.e. using a joystick).

Although various embodiments that incorporate the teachings of the present invention have been shown and described in detail herein, those skilled in the art can readily devise many other varied embodiments that still incorporate these teachings.

The following references are hereby incorporated by reference:

U.S. Pat. No. 7,401,921 Baker et al. "Motorized patient support for eye examination or treatment"

U.S. patent application Ser. No. 13/453,856 filed Apr. 23, 2012 Iyer et al. "Systems and methods for improved ophthalmic imaging"

US Patent Publication No. 2007/0291277 Everett et al. "Spectral domain optical coherence tomography system"

U.S. Pat. No. 7,884,945 Srinivasan et al. "Methods and apparatus for optical coherence tomography scanning"

U.S. Pat. No. 5,847,807 Steinmetz et al. "Arrangement for tiltably journaling an ophthalmologic treatment and/or examining apparatus"

U.S. Pat. No. 4,933,756 Sekine et al. "Eye fundus camera"

Leitgeb et al, "Ultrahigh resolution Fourier domain optical coherence tomography," *Optics Express* 12(10):2156 2004.

We claim:

1. An optical coherence tomography (OCT) device comprising:
    a light source for generating a beam of radiation;
    a beam divider for separating the beam along sample and reference paths;
    a detector for measuring the interference between the radiation in the sample and reference paths;
    an optics head housing optics and opto-mechanical components for scanning the beam over transverse positions within the eye about a pivot point substantially coincident with a location in the pupil, said optics head being independently movable with respect to the eye so that the beam enters the pupil at multiple different entry angles to vary the field of view of the scan;
    a detector for measuring radiation reflected from the eye and generating signals responsive thereto;
    a processor for converting the signals into image information; and
    a driver under the control of the processor for moving the optics head to vary the entry angle while maintaining substantial coincidence between the scanning pivot point and said location in the pupil, said processor collecting signals at each of said multiple entry angles and combining said signals to generate an image, said optics head being movable about a first rotary axis and wherein the first rotary axis is spaced from the pivot point about which the beam is scanned and wherein the driver further adjusts the position of the optics head to insure that the substantial coincidence between the scanning pivot point and the location in the pupil is maintained at each of the multiple entry angles and wherein said further adjustment includes one of (i) a translation of the optics head and (ii) a rotational movement about a second rotary axis.

2. An OCT device as recited in claim 1, wherein the further adjustment is one or more translational movements of the optics head.

3. An OCT device as recited in claim 2, wherein one of the translational movements is in a direction perpendicular to the propagation axis of the beam.

4. An OCT device as recited in claim 1, wherein the further adjustment is a rotational movement of the optics head about a second rotary axis.

5. An OCT device as recited in claim 1, further including a pupil location detector used by the processor to maintain the alignment of the beam on the location in the pupil at each of the multiple entry angles.

6. An OCT device as recited in claim 1, wherein the optics head is movable in the horizontal direction.

7. An OCT device as recited in claim 1, wherein the optics head is movable both horizontally and vertically.

8. An OCT device as recited in claim 1, further comprising one or more fixation targets.

9. An OCT device as recited in claim 1, wherein the total field-of-view of the image is greater than 140 degrees.

10. An OCT device as recited in claim 1, wherein the optics head is mounted to a base which has a patient support that is capable of moving the patient along three orthogonal axes.

11. An OCT device as recited in claim 1, wherein the optics head is mounted to a three axis linear motion stage.

12. An ophthalmic imaging device comprising:
a light source for generating a beam of radiation;
an optics head housing optics, including at least one lens, and opto-mechanical components for scanning the beam over transverse positions within the eye about a pivot point substantially coincident with a location in the pupil, said optics head being independently movable with respect to the eye so that the beam enters the pupil at multiple different entry angles to vary the field of view of the scan, said optics head having an optical axis that is collinear with the pivot point;
a detector for measuring radiation reflected from the eye and generating signals responsive thereto;
a processor for converting the signals into image information; and
a driver under the control of the processor for moving the optics head to vary the entry angle while maintaining substantial coincidence between the scanning pivot point and said location in the pupil, said processor collecting signals at each of said multiple entry angles and combining said signals to generate an image, said optics head being rotatable about a first rotary axis wherein the first rotary axis is arranged to be coincident with the pivot point about which the beam is scanned and wherein the optical alignment of the optics in the optics head is the same for different pupil entry angles.

13. An imaging device as recited in claim 12, further including a pupil location detector used by the processor to maintain the alignment of the beam on the location in the pupil at each of the multiple entry angles.

14. An imaging device as recited in claim 12, wherein the optics head is movable in the horizontal direction.

15. An imaging device as recited in claim 12, wherein the optics head is movable both horizontally and vertically.

16. An imaging device as recited in claim 12, further comprising one or more fixation targets.

17. An imaging device as recited in claim 12, wherein the location in the pupil is the center of the pupil.

18. An imaging device as recited in claim 12, wherein the total field-of-view of the image is greater than 140 degrees.

19. An imaging device as recited in claim 12, wherein the imaging device is a scanning laser ophthalmoscope.

20. An imaging device as recited in claim 12, wherein the imaging device is an optical coherence tomography device.

21. An imaging device as recited in claim 12, wherein the optics head is mounted to a base which has a patient support that is capable of moving the patient along three orthogonal axes.

22. An imaging device as recited in claim 12, wherein the optics head is mounted to a three axis linear motion stage.

* * * * *